Figure 1:
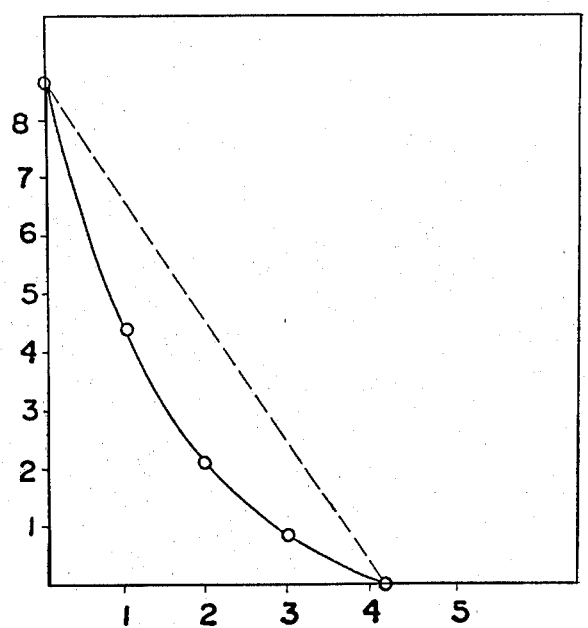

United States Patent [19]

Satomi et al.

[11] 4,401,459
[45] Aug. 30, 1983

[54] HERBICIDAL COMPOSITION HAVING ENHANCED HERBICIDAL ACTIVITY WITH HIGH SELECTIVITY TO SOYBEAN

[75] Inventors: Takeo Satomi; Seizo Sumida, both of Nishinomiya; Ryo Yoshida, Kawanishi, all of Japan

[73] Assignee: Sumitomo Chemical Company, Limited, Osaka, Japan

[21] Appl. No.: 48,730

[22] Filed: Jun. 15, 1979

Related U.S. Application Data

[63] Continuation-in-part of Ser. No. 4,832, Jan. 19, 1979, abandoned.

[30] Foreign Application Priority Data

| Jan. 20, 1978 | [JP] | Japan | 53-5675 |
| Jan. 20, 1978 | [JP] | Japan | 53-5676 |
| Jan. 20, 1978 | [JP] | Japan | 53-5677 |
| Jan. 18, 1979 | [GB] | United Kingdom | 7901849 |
| Jan. 19, 1979 | [BR] | Brazil | 7900363 |

[51] Int. Cl.³ ............. A01N 43/40; A01N 37/38; A01N 37/34; A01N 47/30
[52] U.S. Cl. ................................. 71/94; 71/105; 71/108; 71/109; 71/116; 71/120
[58] Field of Search .............. 71/120, 108, 109, 116, 71/94

[56] References Cited

U.S. PATENT DOCUMENTS 4,129,436 12/1978 Takemoto et al. ............... 71/120

Primary Examiner—Catherine L. Mills
Attorney, Agent, or Firm—Birch, Stewart, Kolasch & Birch

[57] ABSTRACT

A herbicidal composition exerting an enhanced herbicidal activity against various weeds including broad-leaved weeds and Gramineae grasses without any phytotoxicity to soybean, which comprises as an active ingredient N'-[4-(4-methylphenethyloxy)phenyl]-N-methoxy-N-methylurea and as a potentiating agent at least one compound of the formula:

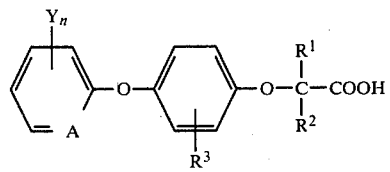

and their salts, esters and amides.

11 Claims, 4 Drawing Figures

HERBICIDAL COMPOSITION HAVING ENHANCED HERBICIDAL ACTIVITY WITH HIGH SELECTIVITY TO SOYBEAN

This is a continuation-in-part application of our co-pending application Ser. No. 4,832 filed Jan. 19, 1979, now abandoned.

The present invention relates to a herbicidal composition having a high selectivity to soybean. More particularly, it relates to a herbicidal composition comprising N'-[4-(4-methylphenethyloxy)phenyl]-N-methoxy-N-methylurea as an essential active ingredient and a certain specific composition as a potentiating agent, which exerts a strongly enhanced herbicidal activity against various weeds without any material phytotoxicity to soybean.

The said N'-[4-(4-methylphenethyloxy)phenyl]-N-methoxy-N-methylurea (hereinafter referred to as "urea") is known (cf. U.S. Pat. No. 4,129,436) and representable by the formula:

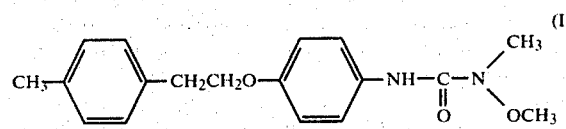

The urea (I) exerts a herbicidal activity against various weeds, particularly broad-leaved weeds, without any appreciable phytotoxicity to soybean. However, its herbicidal activity against Gramineae grasses, particularly grown considerably, is sometimes not sufficient when applied in a small dose or at a low concentration. While its application in a large dose or at a high concentration may produce a sufficient herbicidal activity against Gramineae grasses, there is simultaneously produced a phytotoxicity to soybean.

In order to improve the said drawback as seen on the urea (I), an extensive study has been made. As the result, it has now been found that the use of the urea (I) together with a certain specific compound can eliminate the said drawback and exert a satisfactory herbicidal activity against Gramineae grasses without any material chemical injury to soybean in a small dose or at low concentration.

Accordingly, a basic object of the present invention is to provide a herbicidal composition comprising the urea (I) as an essential active ingredient and a certain specific compound as a potentiating agent, which exerts an enhanced herbicidal activity against various weeds including broad-leaved weeds and Gramineae grasses with a high selectivity to soybean. Another object of this invention is to provide a synergistic compound for the urea (I), which can enhance the herbicidal activity of the latter without affecting unfavorably the high safety of the latter to soybean. A further object of the invention is to provide a method for enhancing the herbicidal activity of the urea (I) without giving any unfavorable influence on its high safety to soybean.

The herbicidal composition of the present invention comprises as an active ingredient the urea (I) and as a potentiating agent at least one of the compounds of the formula:

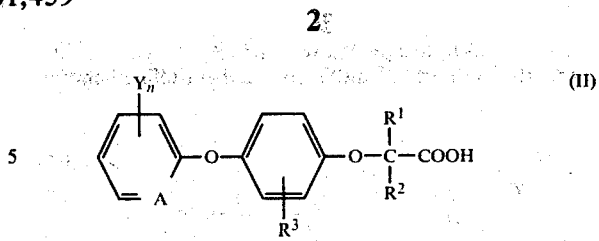

wherein $R^1$ and $R^2$ are each hydrogen, $(C_1-C_4)$alkyl or $(C_1-C_4)$alkoxy, $R^3$ is hydrogen or halogen, A is =C(—Y')— or =N— (in which Y' is hydrogen, halogen, $(C_1-C_4)$alkyl, $(C_1-C_4)$alkoxy, trifluoromethyl or cyano), Y is hydrogen, halogen, $(C_1-C_4)$ alkyl, $(C_1-C_4)$alkoxy, trifluoromethyl or cyano and n is an integer of 1 to 4 (the groups Y being the same or different from each other when n is 2 or more) and their salts, esters and amides.

The compounds useful as the potentiating agents for the urea (I) in this invention generally exert by themselves an excellent herbicidal activity against Gramineae grasses but do not produce any appreciable herbicidal action against broad-leaved weeds.

When the urea (I) is used in combination with the potentiating agent, there is produced a highly enhanced herbicidal activity against a wide variety of herbs including broad-leaved weeds and Gramineae grasses while maintaining a high selectivity to soybean. Particularly notable is that the herbicidal potency produced by the combined use of the urea (I) with the potentiating agent is remarkably higher than that produced by the sole use of the urea (I) or of the potentiating agent. Thus, the production of a synergistic action is recognized in the combined use of the urea (I) with the potentiating agent.

The compounds (II) and their salts, esters and amides usable as the potentiating agents are known (cf. Japanese Patent Publication (unexamined) Nos. 54525/1974, 32730/1976, 139627/1976, 9740/1978 and 15382/1978). Preferred salts are alkali metal salts (e.g. sodium salt, potassium salt). Favorable esters are $(C_1-C_4)$alkyl esters, $(C_1-C_4)$alkoxy$(C_1-C_4)$alkyl esters, phenyl esters, benzyl esters, etc. Esters wherein the hydroxyl group in the carboxyl group is replaced by $(C_1-C_4)$ alkylthio or $(C_3-C_4)$alkenylthio are also favorable. Preferred amides are carbonamides having no substituent at the N-position.

The following compounds are typical examples:

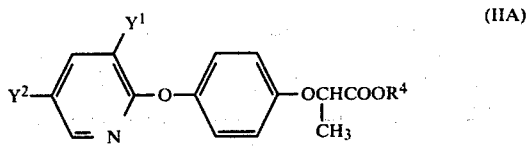

wherein $R^4$ is hydrogen, sodium, potassium or $(C_1-C_4)$alkyl and $Y^1$ and $Y^2$ are each hydrogen, halogen, $(C_1-C_4)$alkyl or trifluoromethyl;

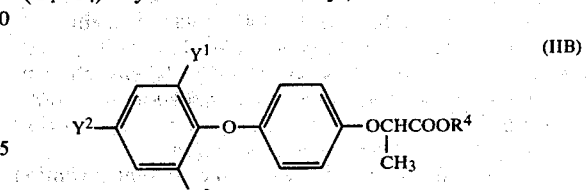

wherein $Y^3$ is hydrogen, halogen, $(C_1-C_4)$alkyl or trifluoromethyl and $R^4$, $Y^1$ and $Y^2$ are each as defined above;

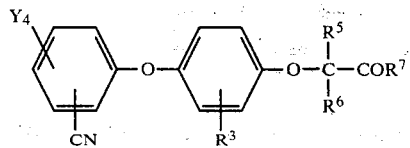 (IIC)

wherein $R^5$ and $R^6$ are each hydrogen or $(C_1-C_4)$alkyl, $R^7$ is hydroxyl, $(C_1-C_4)$alkoxy, $(C_1-C_4)$alkoxy$(C_1-C_4)$alkoxy, phenoxy, benzyloxy, $(C_1-C_4)$alkylthio, $(C_3-C_4)$alkenylthio, amino, —ONa or —OK and $Y^4$ is hydrogen, halogen or trifluoromethyl and $R^3$ is as defined above;

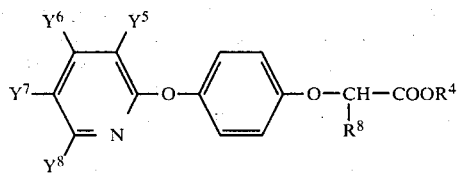 (IID)

wherein $R^8$ is hydrogen or $(C_1-C_4)$alkoxy, $Y^5$ is hydrogen, halogen, $(C_1-C_4)$alkyl or $(C_1-C_4)$alkoxy, $Y^6$ is hydrogen, halogen, cyano or $(C_1-C_4)$alkyl, $Y^7$ is hydrogen, halogen or cyano and $Y^8$ is hydrogen, halogen or $(C_1-C_4)$alkyl, and $R^4$ is as defined above, etc.

More specifically, the following compounds are exemplified as preferred ones:

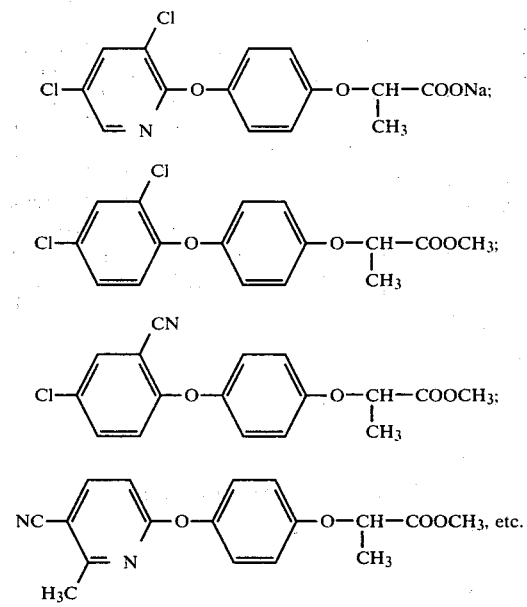

The proportion of the urea (I) and the potentiating agent may be varied within a wide range depending on the kind of the potentiating agent, the kind of the weeds to be exterminated, etc. In order to produce an efficient synergistic action, however, the proportion of the urea (I) and the potentiating agent may be usually 1:0.1–10 by weight, preferably 1:0.3–5 by weight.

The herbicidal composition of the present invention exerts a very strong herbicidal activity against weeds but still shows a high safety to soybean plants. Therefore, it is useful as a selective herbicide, particularly in the field for cultivation of soybean plants.

Examples of the weeds which can be exterminated by the herbicidal composition of the invention include dicotyledonous weeds such as *Chenopodium album, Amaranthus retroflexus,* Polygonum sp., *Stellaria media, Senecio vulgaris, Portulaca oleracea, Xanthium pennsylvanicum, Datura stramonium, Abutilon theophrasti, Ipomea purpurea, Sesbania exaltata, Sida spinosa, Cassia obtusifolia, Galinsoga ciliata* and *Solanum nigram,* and monocotyledonous weeds such as *Eichinochloa crusgalli, Setaria viridis, Digitaria sanguinalis, Panicum dichotomiflorum, Poa annua, Eleucin indica, Bromus tectorum, Avena fatua, Sorghum halepense* and *Agropyron repens.*

Upon practical use, the active ingredient and the potentiating agent may be applied as such to the area where the extermination of weeds is desired. Usually, however, they are formulated in a conventional preparation form such as a dust, granules, fine granules, wettable powder, flowable composition or emulsion so as to be convenient for application. For such formulation, there are normally used solid and/or liquid carriers and/or diluents. Examples of the solid carriers or diluents are mineral powders (e.g. kaolin, bentonite, clay, montmorillonite, talc, diatomaceous earth, mica, vermiculite, gypsum, calcium carbonate, apatite), plant powders (e.g. soybean flour, wheat flour, wood flour, tobacco powder, starch, crystalline cellulose), high molecular weight compounds (e.g. petroleum resin, polyvinyl chloride, dammar gum, ketone resin), alumina, wax, etc. Examples of the liquid carriers or diluents are alcohols (e.g. methanol, ethanol, ethylene glycol, benzyl alcohol), aromatic hydrocarbons, (e.g. benzene, toluene, xylene, methylnaphthalene), chlorinated hydrocarbons (e.g. chloroform, carbon tetrachloride, monochlorobenzene), ethers (e.g. dioxane, tetrahydrofuran), ketones (e.g. acetone, methylethylketone, cyclohexanone), esters (e.g. ethyl acetate, butyl acetate, ethylene glycol acetate), acid amides (e.g. dimethylformamide), nitriles (e.g. acetonitrile), ether alcohols (e.g. ethylene glycol ethyl ether), water, etc. In addition, surfactants may be employed for the purpose of emulsifying, dispersing, spreading and the like. The surfactants may be non-ionic, anionic, cationic or amphoteric, and their specific examples are polyoxyethylene alkyl ether, polyoxyethylene alkyl aryl ether, polyoxyethylene fatty acid ester, sorbitan fatty acid ester, polyoxyethylene sorbitan fatty acid ester, ethylene oxide polymer, propylene oxide polymer, polyoxyethylene alkyl phosphate, fatty acid salts, alkylsulfates, alkylsulfonates, alkylarylsulfonates, alkylphosphates, polyoxyethylene alkylsulfates, etc. Moreover, other conventional aids such as gelatin, casein, sodium alginate, starch, agar and polyvinyl alcohol may be optionally employed.

The herbicidal composition of the invention may optionally comprise, in addition to the said essential active ingredients, other herbicides, antibiotic pesticides, pyrethroidal insecticides, other insecticides, fungicides, fertilizers, etc.

The concentration of the urea (I) as the active ingredient in the herbicidal composition may be usually from 0.01 to 90% by weight, preferably from 1 to 50% by weight. The potentiating agent may be included in an amount of 0.1 to 10 parts by weight, preferably 0.3 to 5 parts by weight to one part by weight of the urea (I).

Some typical examples of the herbicidal composition of the invention are illustratively shown below. In these examples, part(s) are by weight.

EXAMPLE A

Wettable powder:

The compound (I) (25 parts), the compound (IIa), (IIb), (IIc) or (IId) (25 parts), an alkylbenzenesulfonate (5 parts) as a wetting agent and diatomaceous earth (45 parts) were pulverized and mixed together to make a wettable powder preparation.

EXAMPLE B

Emulsion:

The compound (I) (10 parts), the compound (IIa), (IIb), (IIc) or (IId) (3 parts), cyclohexanone (37 parts), dimethylformamide (30 parts) and an emulsifier "Toxanon P-8-L" (trademark; manufactured by Sanyo Kasei K.K.) (20 parts) were mixed together to make an emulsion preparation.

EXAMPLE C

Dust:

The compound (I) (2 parts), the compound (IIa), (IIb), (IIc) or (IId) (10 parts) and clay (88 parts) were pulverized and mixed together to make a dust preparation.

EXAMPLE D

Granule:

The compound (I) (2.5 parts), the compound (IIa), (IIb), (IIc) or (IId) (2.5 parts), a ligninsulfonate (7 parts) and clay (38 parts) were pulverized and mixed together. The resulting mixture was admixed with water, kneaded well, granulated and dried to give a granular preparation.

Application of the herbicidal composition of the invention may be made before or after appearance of weeds or grasses to be exterminated. However, the application after the apperance is generally preferred. The amount of the herbicidal composition to be applied may be from 5 to 50 g (as the active ingredient) per are, preferably from 3 to 30 g per are.

In order to demonstrate the excellent effect of the herbicidal composition of the invention, some of the test results are shown in the examples as hereinafter set forth.

When two herbicidal compositions are used in combination, the herbicidal activity expected to be produced therefrom can be calculated according to the following equation (S. R. Colby: Weeds, 15, 20-22 (1967)):

$$E = X + Y - \frac{X \cdot Y}{100} \quad (A)$$

wherein X is the growth prevention percentage (%) when one of the herbicides is employed solely in an amount of p (g/are), Y is the growth prevention percentage (%) when the other herbicide is employed solely in an amount of q (g/are) and E is the growth prevention percentage (%) expected to be produced when the herbicides are employed together in amounts of p (g/are) and q (g/are), respectively. When the actually produced growth prevention is higher than the calculated value (E), the production of a synergistic action may be affirmed.

Example 1 (Herbicidal Effect)

Wagner's pots (1/2000 are) were each filled with upland soil, and the seeds of black nightshade (*Solanum nigram*), common morningglory (*Ipomea purpurea*), green foxtail (*Setaria viridis*) and Johnsongrass (*Sorghum halepense*) were separately sowed in the pots and grown outdoors for 20 days. Thereafter, a wettable powder preparation comprising the test compound(s) was dispersed in water with a wetting agent for application at a volume of 3 liters per are, and the resultant mixture was sprayed to the foliage of the test plants over the top by means of a small hand sprayer. At this foliar application, black nightshade was in the 2-leaf stage, common morningglory in the 2-leaf stage, green foxtail in the 3.5-leaf stage and Johnsongrass in the 3-leaf stage. Thus, the test plants were grown outdoors for a additional 20 days, and the herbicidal effect was examined. The herbicidal effect was represented by the growth prevention percentage calculated according to the following formula:

$$\text{Growth prevention percentage (\%)} = \left(1 - \frac{\text{Fresh weight of test plants in treated plot}}{\text{Fresh weight of test plants in untreated plot}}\right) \times 100$$

The results are shown in Tables 1 to 4, wherein the values in parenthesis indicate the calculated ones according to the said equation (A).

TABLE 1

(Herbicidal effect on black nightshade)

| Amount of Urea (I) (g/are) | Amount of potentiating agent (g/are) | | Growth prevention percentage (%) | Amount of Urea (I) (g/are) | Amount of potentiating agent (g/are) | | Growth prevention percentage (%) |
|---|---|---|---|---|---|---|---|
| 0 | (IIa) | 0 | 0 | 0 | (IIc) | 0 | 0 |
|  |  | 3 | 0 |  |  | 3 | 0 |
|  |  | 6 | 0 |  |  | 6 | 0 |
|  |  | 10 | 0 |  |  | 10 | 0 |
| 2 | (IIa) | 0 | 43 | 2 | (IIc) | 0 | 43 |
|  |  | 3 | 95(43) |  |  | 3 | 65(43) |
|  |  | 6 | 100(43) |  |  | 6 | 80(43) |
|  |  | 10 | 100(43) |  |  | 10 | 93(43) |
| 4 | (IIa) | 0 | 92 | 4 | (IIc) | 0 | 92 |
|  |  | 3 | 100(92) |  |  | 3 | 96(92) |
|  |  | 6 | 100(92) |  |  | 6 | 99(92) |
|  |  | 10 | 100(92) |  |  | 10 | 100(92) |
| 8 | (IIa) | 0 | 100 | 8 | (IIc) | 0 | 100 |
|  |  | 3 | 100(100) |  |  | 3 | 100(100) |
|  |  | 6 | 100(100) |  |  | 6 | 100(100) |
|  |  | 10 | 100(100) |  |  | 10 | 100(100) |
| 0 | (IIb) | 0 | 0 | 0 | (IId) | 0 | 0 |
|  |  | 3 | 0 |  |  | 2 | 0 |
|  |  | 6 | 0 |  |  | 4 | 0 |
|  |  | 10 | 0 |  |  | 8 | 0 |
| 2 | (IIb) | 0 | 43 | 2 | (IId) | 0 | 43 |
|  |  | 3 | 93(43) |  |  | 2 | 90(43) |
|  |  | 6 | 100(43) |  |  | 4 | 95(43) |
|  |  | 10 | 100(43) |  |  | 8 | 100(43) |
| 4 | (IIb) | 0 | 92 | 4 | (IId) | 0 | 92 |
|  |  | 3 | 98(92) |  |  | 2 | 100(92) |
|  |  | 6 | 100(92) |  |  | 4 | 100(92) |
|  |  | 10 | 100(92) |  |  | 10 | 100(92) |
| 8 | (IIb) | 0 | 100 | 8 | (IId) | 0 | 100 |
|  |  | 3 | 100(100) |  |  | 2 | 100(100) |
|  |  | 6 | 100(100) |  |  | 4 | 100(100) |
|  |  | 10 | 100(100) |  |  | 8 | 100(100) |

TABLE 2

(Herbicidal effect on common morningglory)

| Amount of Urea (I) (g/are) | Amount of potentiating agent (g/are) | | Growth prevention percentage (%) | Amount of Urea (I) (g/are) | Amount of potentiating agent (g/are) | | Growth prevention percentage (%) |
|---|---|---|---|---|---|---|---|
| 0 | (IIa) | 0 | 0 | 0 | (IIc) | 0 | 0 |
|  |  | 3 | 0 |  |  | 3 | 0 |
|  |  | 6 | 0 |  |  | 6 | 0 |
|  |  | 10 | 0 |  |  | 10 | 0 |
| 2 | (IIa) | 0 | 22 | 2 | (IIc) | 0 | 22 |
|  |  | 3 | 90(22) |  |  | 3 | 45(22) |
|  |  | 6 | 94(22) |  |  | 6 | 70(22) |
|  |  | 10 | 97(22) |  |  | 10 | 90(22) |
| 4 | (IIa) | 0 | 68 | 4 | (IIc) | 0 | 68 |
|  |  | 3 | 93(68) |  |  | 3 | 90(68) |
|  |  | 6 | 98(68) |  |  | 6 | 95(68) |
|  |  | 10 | 100(68) |  |  | 10 | 100(68) |
| 8 | (IIa) | 0 | 93 | 8 | (IIc) | 0 | 93 |
|  |  | 3 | 98(93) |  |  | 3 | 98(93) |
|  |  | 6 | 100(93) |  |  | 6 | 100(93) |
|  |  | 10 | 100(93) |  |  | 10 | 100(93) |
| 0 | (IIb) | 0 | 0 | 0 | (IId) | 0 | 0 |
|  |  | 3 | 0 |  |  | 2 | 0 |
|  |  | 6 | 0 |  |  | 4 | 0 |
|  |  | 10 | 0 |  |  | 8 | 0 |
| 2 | (IIb) | 0 | 22 | 2 | (IId) | 0 | 22 |
|  |  | 3 | 90(22) |  |  | 2 | 45(22) |
|  |  | 6 | 94(22) |  |  | 4 | 100(22) |
|  |  | 10 | 96(22) |  |  | 8 | 100(22) |
| 4 | (IIb) | 0 | 68 | 4 | (IId) | 0 | 68 |
|  |  | 3 | 93(68) |  |  | 2 | 93(68) |
|  |  | 6 | 95(68) |  |  | 4 | 100(68) |
|  |  | 10 | 100(68) |  |  | 8 | 100(68) |
| 8 | (IIb) | 0 | 93 | 8 | (IId) | 0 | 93 |
|  |  | 3 | 100(93) |  |  | 2 | 100(93) |
|  |  | 6 | 100(93) |  |  | 4 | 100(93) |
|  |  | 10 | 100(93) |  |  | 8 | 100(93) |

TABLE 3

(Herbicidal effect on green foxtail)

| Amount of Urea (I) (g/are) | Amount of potentiating agent (g/are) | | Growth prevention percentage (%) | Amount of Urea (I) (g/are) | Amount of potentiating agent (g/are) | | Growth prevention percentage (%) |
|---|---|---|---|---|---|---|---|
| 0 | (IIa) | 0 | 0 | 0 | (IIc) | 0 | 0 |
|  |  | 3 | 41 |  |  | 3 | 35 |
|  |  | 6 | 82 |  |  | 6 | 80 |
|  |  | 10 | 97 |  |  | 10 | 100 |
| 2 | (IIa) | 0 | 18 | 2 | (IIc) | 0 | 18 |
|  |  | 3 | 85(52) |  |  | 3 | 75(46) |
|  |  | 6 | 100(85) |  |  | 6 | 100(83) |
|  |  | 10 | 100(98) |  |  | 10 | 100(100) |
| 4 | (IIa) | 0 | 25 | 4 | (IIc) | 0 | 25 |
|  |  | 3 | 97(55) |  |  | 3 | 90(55) |
|  |  | 6 | 100(85) |  |  | 6 | 100(85) |
|  |  | 10 | 100(98) |  |  | 10 | 100(100) |
| 8 | (IIa) | 0 | 52 | 8 | (IIc) | 0 | 52 |
|  |  | 3 | 100(72) |  |  | 3 | 100(77) |
|  |  | 6 | 100(91) |  |  | 6 | 100(90) |
|  |  | 10 | 100(99) |  |  | 10 | 100(100) |
| 0 | (IIb) | 0 | 0 | 0 | (IId) | 0 | 0 |
|  |  | 3 | 33 |  |  | 2 | 45 |
|  |  | 6 | 82 |  |  | 4 | 90 |
|  |  | 10 | 100 |  |  | 8 | 100 |
| 2 | (IIb) | 0 | 18 | 2 | (IId) | 0 | 18 |
|  |  | 3 | 90(45) |  |  | 2 | 80(54) |
|  |  | 6 | 100(85) |  |  | 4 | 100(91) |
|  |  | 10 | 100(100) |  |  | 8 | 100(100) |
| 4 | (IIb) | 0 | 25 | 4 | (IId) | 0 | 25 |
|  |  | 3 | 93(50) |  |  | 2 | 95(58) |
|  |  | 6 | 100(86) |  |  | 4 | 100(92) |
|  |  | 10 | 100(100) |  |  | 8 | 100(100) |
| 8 | (IIb) | 0 | 52 | 8 | (IId) | 0 | 52 |
|  |  | 3 | 100(68) |  |  | 2 | 100(73) |
|  |  | 6 | 100(91) |  |  | 4 | 100(95) |
|  |  | 10 | 100(100) |  |  | 8 | 100(100) |

TABLE 4

(Herbicidal effect on Johnsongrasse)

| Amount of Urea (I) (g/are) | Amount of potentiating agent (g/are) | | Growth prevention percentage (%) | Amount of Urea (I) (g/are) | Amount of potentiating agent (g/are) | | Growth prevention percentage (%) |
|---|---|---|---|---|---|---|---|
| 0 | (IIa) | 0 | 0 | 0 | (IIc) | 0 | 0 |
|  |  | 3 | 31 |  |  | 3 | 30 |
|  |  | 6 | 72 |  |  | 6 | 67 |
|  |  | 10 | 100 |  |  | 10 | 89 |
| 2 | (IIa) | 0 | 18 | 2 | (IIc) | 0 | 18 |
|  |  | 3 | 90(43) |  |  | 3 | 70(42) |
|  |  | 6 | 97(77) |  |  | 6 | 95(72) |
|  |  | 10 | 100(100) |  |  | 10 | 100(90) |
| 4 | (IIa) | 0 | 22 | 4 | (IIc) | 0 | 22 |
|  |  | 3 | 95(46) |  |  | 3 | 85(45) |
|  |  | 6 | 100(78) |  |  | 6 | 100(75) |
|  |  | 10 | 100(100) |  |  | 10 | 100(91) |
| 8 | (IIa) | 0 | 43 | 8 | (IIc) | 0 | 43 |
|  |  | 3 | 100(61) |  |  | 3 | 90(60) |
|  |  | 6 | 100(94) |  |  | 6 | 100(81) |
|  |  | 10 | 100(100) |  |  | 10 | 100(93) |
| 0 | (IIb) | 0 | 0 | 0 | (IId) | 0 | 0 |
|  |  | 3 | 21 |  |  | 2 | 50 |
|  |  | 6 | 62 |  |  | 4 | 92 |
|  |  | 10 | 97 |  |  | 8 | 100 |
| 2 | (IIb) | 0 | 18 | 2 | (IId) | 0 | 18 |
|  |  | 3 | 72(35) |  |  | 2 | 75(59) |
|  |  | 6 | 84(69) |  |  | 4 | 100(93) |
|  |  | 10 | 100(98) |  |  | 8 | 100(100) |
| 4 | (IIb) | 0 | 22 | 4 | (IId) | 0 | 22 |
|  |  | 3 | 97(38) |  |  | 2 | 90(61) |
|  |  | 6 | 100(70) |  |  | 4 | 100(93) |
|  |  | 10 | 100(98) |  |  | 8 | 100(100) |
| 8 | (IIb) | 0 | 43 | 8 | (IId) | 0 | 43 |
|  |  | 3 | 98(55) |  |  | 2 | 100(71) |
|  |  | 6 | 100(78) |  |  | 4 | 100(95) |
|  |  | 10 | 100(98) |  |  | 8 | 100(100) |

As seen in the above results, the growth prevention actually produced by the combined use of the urea (I) with the potentiating agent is higher than the calculated growth prevention, and therefore the production of a real synergistic effect may be recognized.

Example 2 (Analysis of herbicidal effect)

Figure 2:
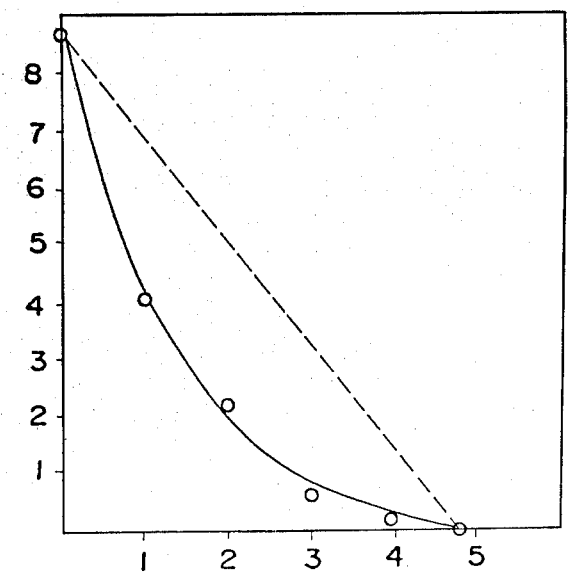
Figure 3:
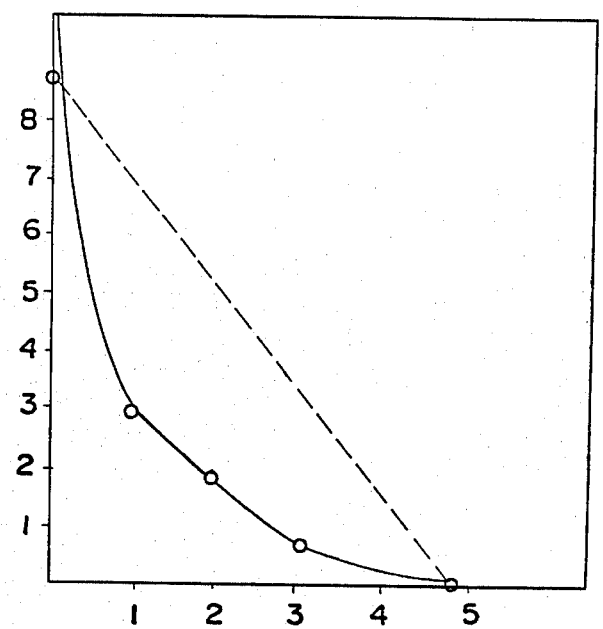
Figure 4:
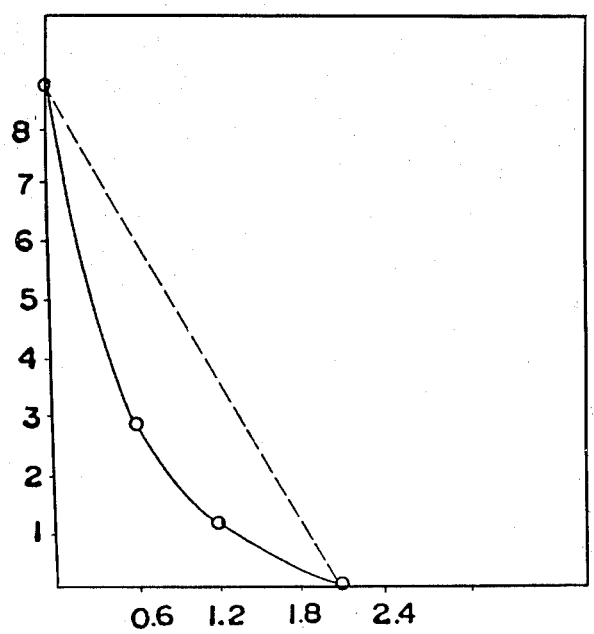

Cultivation of Johnsongrass (Sorghum halepense) as the test plants, treatment with the test compound(s) and calculation of the growth prevention percentage were carried out as in Example 1. The results with the combinations of the urea (I) and the potentiating agent (IIa), of the urea (I) and the potentiating agent (IIb), of the urea (I) and the potentiating agent (IIc) and of the urea (I) and the potentiating agent (IId) are respectively shown in Tables 5 to 8. Further, 50% growth preventions obtained from the said results are plotted on graphs to give respectively FIGS. 1 to 4 of the accompanying drawings, the abscissa and the ordinate of each graph representing respectively the applied weight (gram) of the potentiating agent per are and the applied weight (gram) of the urea (I).

As seen in these figures, the equivalent effect line (solid line) is present below the arithmetically summed effect line (dotted line), and therefore the production of a real synergistic effect may be recognized (cf. H. Chisaka: Zasso Kenkyu (Study of weeds), 14, 12–18 (1972)).

TABLE 5

| Amount of potentiating agent (IIa) (g/are) | Amount of Urea (I) (g/are) | | | | |
|---|---|---|---|---|---|
| | 0 | 1.5 | 3 | 4.5 | 6 | 8 |
| 0 | 0 | 10 | 15 | 25 | 33 | 43 |
| 1 | 11 | 31 | 41 | 52 | 83 | — |
| 2 | 18 | 40 | 58 | 84 | — | — |
| 3 | 31 | 61 | 91 | — | — | — |
| 4 | 49 | 90 | — | — | — | — |
| 5 | 62 | — | — | — | — | — |

TABLE 6

| Amount of potentiating agent (IIb) (g/are) | Amount of Urea (I) (g/are) | | | | |
|---|---|---|---|---|---|
| | 0 | 1.5 | 3 | 4.5 | 6 | 8 |
| 0 | 0 | 10 | 15 | 25 | 33 | 43 |
| 1 | 5 | 21 | 41 | 58 | 71 | — |
| 2 | 11 | 40 | 62 | 82 | — | — |
| 3 | 21 | 71 | 83 | — | — | — |
| 4 | 40 | 80 | — | — | — | — |
| 5 | 52 | — | — | — | — | — |

TABLE 7

| Amount of potentiating agent (IIc) (g/are) | Amount of Urea (I) (g/are) | | | | |
|---|---|---|---|---|---|
| | 0 | 1.5 | 3 | 4.5 | 6 | 8 |
| 0 | 0 | 10 | 15 | 25 | 33 | 43 |
| 1 | 13 | 30 | 52 | 67 | 75 | 80 |
| 2 | 19 | 43 | 72 | 82 | 90 | — |
| 3 | 30 | 61 | 80 | 95 | — | — |
| 4 | 38 | 72 | 90 | — | — | — |
| 5 | 52 | 79 | — | — | — | — |

TABLE 8

| Amount of potentiating agent (IId) (g/are) | Amount of Urea (I) (g/are) | | | | |
|---|---|---|---|---|---|
| | 0 | 1.5 | 3 | 4.5 | 6 | 8 |
| 0 | 0 | 10 | 15 | 25 | 33 | 43 |
| 0.6 | 20 | 43 | 52 | 60 | 75 | — |
| 1.2 | 31 | 60 | 75 | 90 | — | — |
| 1.8 | 45 | 72 | 85 | — | — | — |
| 2.4 | 65 | 80 | — | — | — | — |

Example 3 (Test on herbicidal effect in soybean cultivating field)

To the field, each plot having an area of 4 m$^2$, soybean as a crop plant and common cocklebur (*Xanthium pennsylvanicum*), common morningglory (*Ipomea purpurea*), redroot pigweed (*Amaranthus retroflexus*), large crabgrass (*Digitaria sanguinalis*) and green foxtail (*Setaria viridis*) as weeds were sowed. After 2 weeks, a designed amount of the test compound(s) was applied to the foliage of the test plants over the top by the aid of a small sprayer. At the foliar application, common cocklebur was at the 2 to 3-leaf stage, common morningglory at the 2 to 3-leaf stage, redroot pigweed at the 2 to 3-leaf stage, large crabgrass at the 4 to 5-leaf stage and green foxtail at the 4 to 5-leaf stage. Thereafter, cultivation was carried out for 1 month, and then the phytotoxicity and the herbicidal effect were observed. The growth prevention percentage was calculated as in Example 1. The test compound(s) were used in the form of a wettable powder preparation or in the form of the sodium salt, and they were dispersed in water for application at a volume of 3 liters per are with addition of a wetting agent. The test was effected in 3 replica. The results are shown in Table 9.

TABLE 9

| No. | Test compounds | | Phytotoxicity Soybean | Growth prevention percentage (%) | | | | |
|---|---|---|---|---|---|---|---|---|
| | | | | Common cocklebur | Common morningglory | Redroot pigweed | Large crabgrass | Green foxtail |
| 1 | Urea (I) + (7 g/a) | Potentiating agent (IIa) (10 g/a) | 0 | 100 | 100 | 100 | 100 | 100 |
| 2 | Urea (I) + (7 g/a) | Potentiating agent (IIa) (5 g/a) | 0 | 100 | 100 | 100 | 100 | 100 |
| 3 | Urea (I) + (7 g/a) | Potentiating agent (IId) (10 g/a) | 0 | 100 | 100 | 100 | 100 | 100 |
| 4 | Urea (I) + (7 g/a) | Potentiating agent (IId) (5 g/a) | 0 | 100 | 100 | 100 | 100 | 100 |
| 5 | Bentazon + (7 g/a) | Potentiating agent [A]* (15 g/a) | 30 | 100 | 90 | 0 | 5 | 10 |
| 6 | Bentazon + (7 g/a) | Potentiating agent [A] (7 g/a) | 15 | 100 | 85 | 0 | 0 | 5 |
| 7 | Urea (I) (7 g/a) | | 0 | 100 | 98 | 100 | 46 | 62 |
| 8 | Bentazon (7 g/a) | | 0 | 100 | 85 | 60 | 5 | 0 |
| 9 | Potentiating agent [A] (15 g/a) | | 0 | 0 | 0 | 30 | 92 | 85 |
| 10 | Potentiating agent [A] (7 g/a) | | 0 | 0 | 0 | 20 | 80 | 74 |
| 11 | Potentiating agent (IIa) (10 g/a) | | 0 | 0 | 5 | 20 | 100 | 100 |
| 12 | Potentiating agent (IIa) (5 g/a) | | 0 | 0 | 0 | 0 | 100 | 100 |
| 13 | Potentiating agent (IId) (10 g/a) | | 0 | 0 | 0 | 0 | 100 | 100 |
| 14 | Potentiating agent (IId) (5 g/a) | | 0 | 0 | 0 | 0 | 100 | 100 |

Note:
*2-(1-Allyloxyamino)butylidene-5,5-dimethyl-4-methoxycarbonyl-cyclohexane-1,3-dione sodium salt.

From the above results, it is seen that the combined application of the urea (I) and the potentiating agent exert a remarkable herbicidal activity not only on broad-leaved weeds but also on Gramineae grasses, while the sole application of the urea (I) or of the potentiating agent shows a certain herbicidal activity only on either one of them. It is also seen that the synergistic effect is produced only between the urea (I) and the potentiating agent.

What is claimed is:

1. A herbicidal composition which consists essentially of an effective herbicidal amount of N'-[4-(4-methylphenethyloxy)phenyl]-N-methoxy-N-methylurea as an active ingredient and as a potentiating agent at least one of the compounds of the formula:

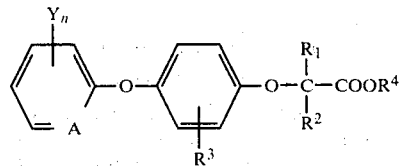

wherein $R^1$ and $R^2$ are each hydrogen, $(C_1-C_4)$alkyl or $(C_1-C_4)$ alkoxy, $R^3$ is hydrogen or halogen, $R^4$ is hydrogen, sodium, potassium or $(C_1-C_4)$alkyl, A is $=C(-Y')-$ or $=N-$ in which Y' is hydrogen, halogen, $(C_1-C_4)$alkyl, $(C_1-C_4)$alkoxy, or trifluoromethyl, Y is hydrogen, halogen, $(C_1-C_4)$alkyl, $(C_1-C_4)$alkoxy or trifluoromethyl and n is an integer of 1 to 4, the Y groups being the same or different from each other when n is 2 or more, the proportion of active ingredient to potentiating agent being 1 : 0.3–5 by weight in said composition.

2. The herbicidal composition according to claim 1, wherein the potentiating agent is a compound of the formula:

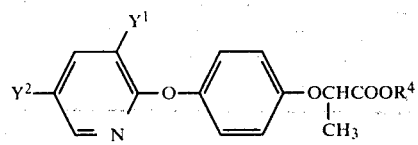

wherein $R^4$ is hydrogen, sodium, potassium or $(C_1-C_4)$alkyl and $Y^1$ and $Y^2$ are each hydrogen, halogen, $(C_1-C_4)$alkyl or trifluoromethyl.

3. The herbicidal composition according to claim 2, wherein the potentiating agent is a compound of the formula:

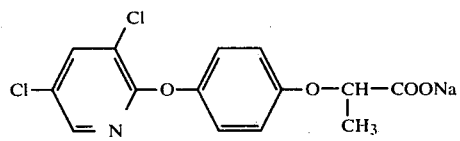

4. The herbicidal composition according to claim 1, wherein the concentration of the active ingredient is from 0.01 to 90% by weight.

5. The herbicidal composition according to claim 1, which further comprises at least one carrier and/or diluent.

6. A herbicidal composition which consists essentially of an effective herbicidal amount of N'-[4-(4-methylphenethyloxy)phenyl]-N-methoxy-N-methylurea as an active ingredient and as a potentiating agent a compound of the formula:

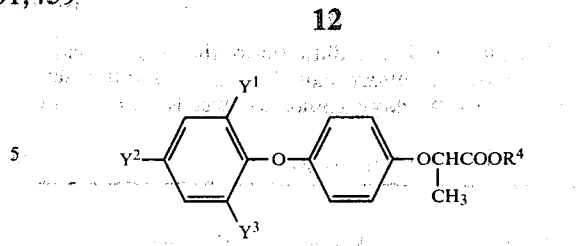

wherein $R^4$ is hydrogen, sodium, potassium or $(C_1-C_4)$alkyl and $Y^1$, $Y^2$ and $Y^3$ are each hydrogen, halogen, $(C_1-C_4)$alkyl or trifluoromethyl, the proportion of active ingredient to potentiating agent being 1 : 0.3–5 by weight in said composition.

7. The herbicidal composition according to claim 6, wherein the potentiating agent is a compound of the formula:

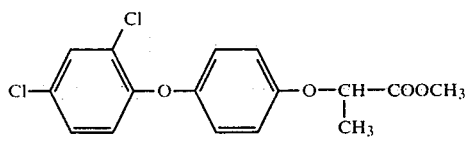

8. The herbicidal composition according to claim 6, wherein the potentiating agent is a compound of the formula:

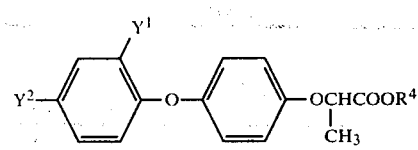

wherein $R^4$ is hydrogen, sodium, potassium or $(C_1-C_4)$alkyl and $Y^1$ and $Y^2$ are each halogen.

9. A method for exterminating weeds in a field where soybean is cultivated, which comprises applying thereto a herbicidally effective amount of the compound N'-[4-(4-methylphenethyloxy)phenyl]-N-methoxy-N-methylurea together with a sufficient amount of a potentiating agent to enhance the herbicidal activity of said compound, said potentiating agent being at least one of the compounds of the formula:

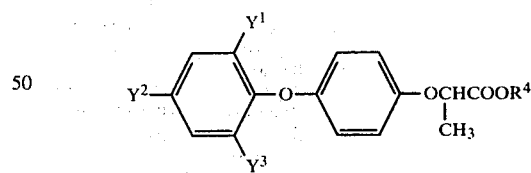

wherein $R^4$ is hydrogen, sodium, potassium or $(C_1-C_4)$alkyl and $Y^1$, $Y^2$ and $Y^3$ are each hydrogen, halogen, $(C_1-C_4)$alkyl or trifluoromethyl.

10. The method according to claim 9, wherein the N'-[4-(4-methylphenethyloxy)phenyl]-N-methoxy-N-methylurea and the potentiating agent are applied in a proportion of 1 : 0.3–5 by weight.

11. The method according to claim 9, wherein the N'-[4-(4-methylphenethyloxy)phenyl]-N-methoxy-N-methylurea is applied in an amount of from 3 to 30 g/are.

* * * * *